United States Patent [19]
McCulloch et al.

[11] Patent Number: 5,276,246
[45] Date of Patent: Jan. 4, 1994

[54] PROCESS FOR SEPARATING NORMAL OLEFINS FROM NON-NORMAL OLEFINS

[75] Inventors: Beth McCulloch, Clarendon Hills; James R. Lansbarkis, Wood Dale, both of Ill.

[73] Assignee: UOP, Des Plaines, Ill.

[21] Appl. No.: 811,864

[22] Filed: Dec. 23, 1991

[51] Int. Cl.$^5$ .............................. C07C 7/13
[52] U.S. Cl. ...................... 585/829; 585/820; 585/826
[58] Field of Search ............ 585/829, 809, 820, 826

[56] References Cited

U.S. PATENT DOCUMENTS

| | | | |
|---|---|---|---|
| 2,985,589 | 5/1961 | Broughton et al. | 210/34 |
| 3,040,777 | 6/1962 | Carson et al. | 137/625.15 |
| 3,422,848 | 1/1969 | Liebman et al. | 137/625.15 |
| 3,706,812 | 12/1972 | De Rosset et al. | 260/674 SA |
| 3,723,561 | 3/1973 | Priegnitz | 585/820 |
| 4,061,724 | 12/1977 | Grose et al. | 423/355 |
| 4,073,865 | 2/1978 | Flanigen et al. | 423/339 |
| 4,085,158 | 4/1978 | Dixon et al. | 585/670 |
| 4,104,294 | 8/1978 | Grose et al. | 260/448 C |
| 4,119,678 | 10/1978 | Neuzil et al. | 585/829 |
| 4,309,281 | 1/1982 | Dessau | 208/310 |
| 4,444,986 | 4/1984 | Dessau | 585/829 |
| 4,455,445 | 6/1984 | Neuzil et al. | 585/820 |
| 4,486,618 | 12/1984 | Kulprathipanja et al. | 585/829 |
| 4,556,461 | 12/1985 | Ogura et al. | 585/809 |
| 4,642,397 | 2/1987 | Zinnen et al. | 568/934 |

FOREIGN PATENT DOCUMENTS

| | | |
|---|---|---|
| 0372938 | 6/1990 | European Pat. Off. . |
| 0372939 | 6/1990 | European Pat. Off. . |

OTHER PUBLICATIONS

"Silicalite, A New Hydrophobic Crystalline Silica Molecular Sieve;" Nature, vol. 271, Feb. 9, 1978.

*Primary Examiner*—Anthony McFarlane
*Attorney, Agent, or Firm*—Thomas K. McBride; John F. Spears, Jr.; Jack H. Hall

[57] ABSTRACT

A chromatographic process for separating normal olefins from mixtures with branched-chain olefins with a high silica zeolitic molecular sieve, e.g., silicalites, ZSM-5, etc., having low acid catalytic reactivity, which selectively adsorbs the normal olefins, and uses alkyl-substituted cycloparaffins, e.g., methylcyclohexane, as desorbents.

9 Claims, 2 Drawing Sheets

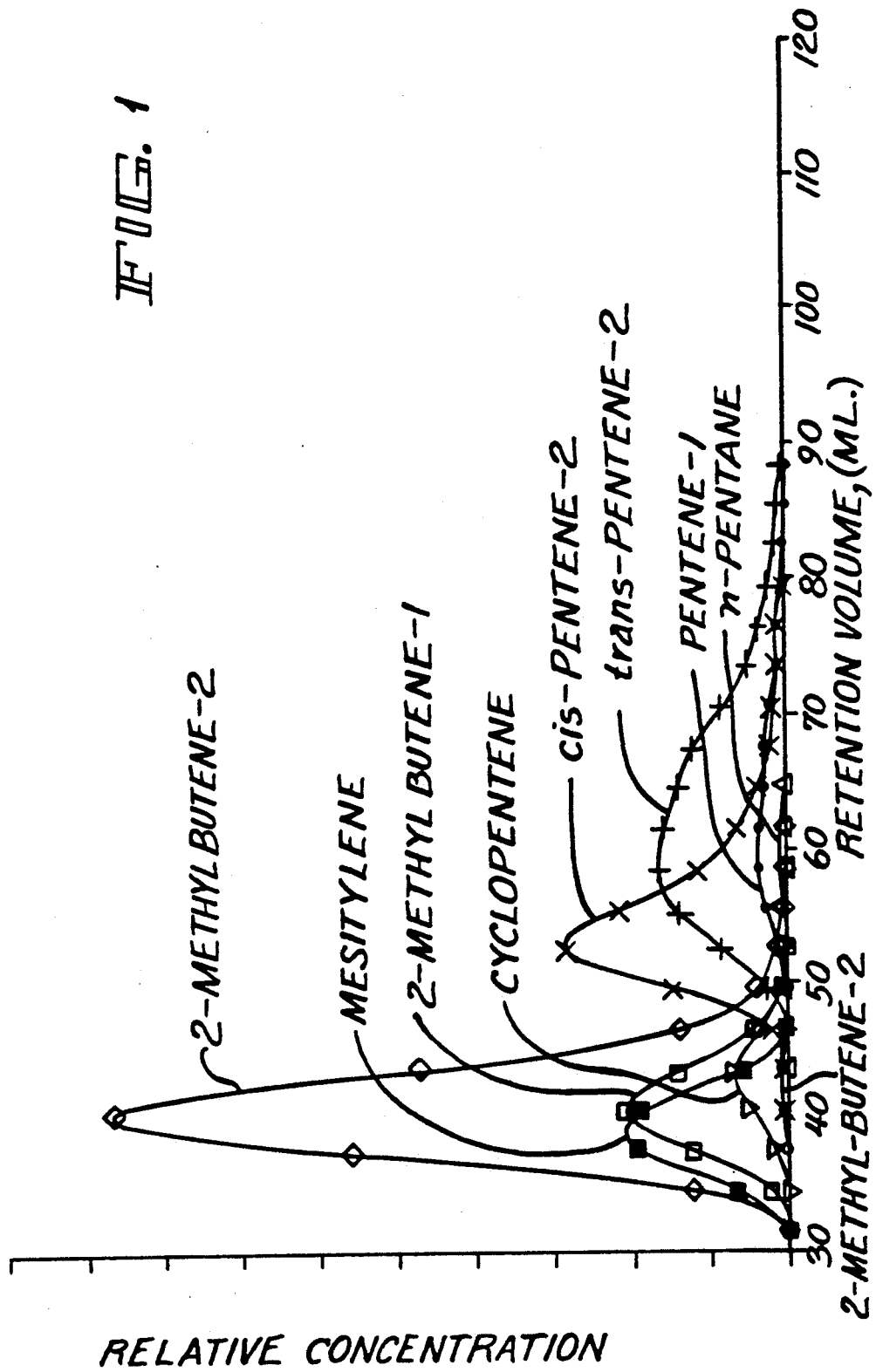

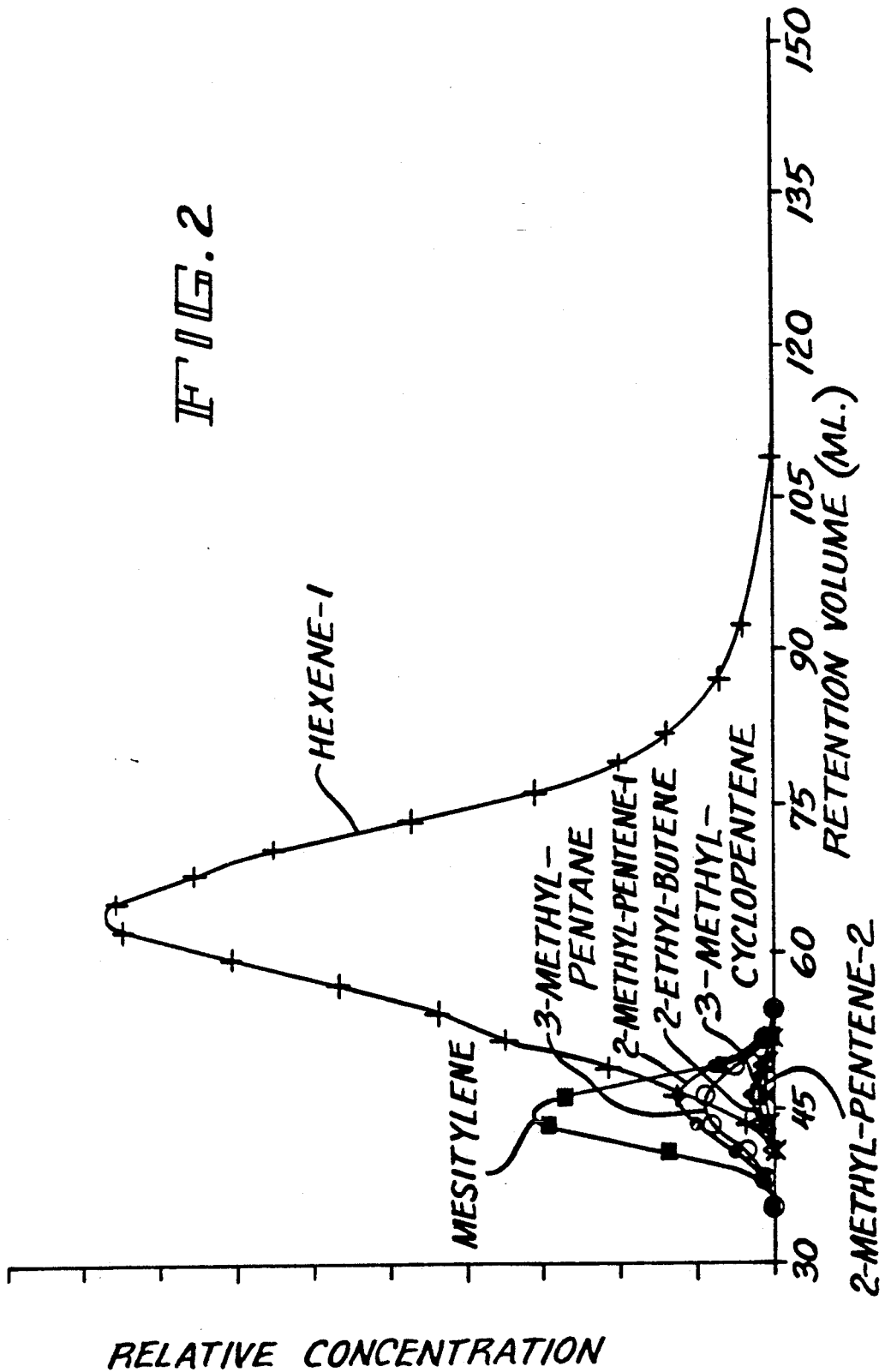

PROCESS FOR SEPARATING NORMAL OLEFINS FROM NON-NORMAL OLEFINS

FIELD OF THE INVENTION

The field of art to which this invention pertains in the separation of normal $C_5$ to $C_8$ olefins from mixtures thereof with non-normal $C_5$ to $C_8$ olefins.

BACKGROUND OF THE INVENTION

The separation of many classes of compounds by selective adsorption is well known. Also, separations of various mixtures containing olefins into their components are known, e.g., the preferential adsorption of linear olefins over branched olefins using adsorbents such as ZSM-5 and silicalite from Dessau U.S. Pat. No. 4,309,281; the separation of normal $C_4$ olefins from isobutylene with silicalite and pentene-1 as desorbent from Neuzil et al U.S. Pat. No. 4,455,445 and the separation of normal $C_6$ olefins from branched-chain and/or cyclic olefin hydrocarbons with silicalite and pentene-1 or butene-1 as desorbent from Kulprathipanja et al U.S. Pat. No. 4,486,618.

European Patent Applications 0 372 938 and 0 372 939 disclose a method for treating silicalite or ZSM-5 zeolites to enable the treated adsorbents to selectively adsorb n-olefins and n-paraffins from mixtures thereof with branched olefins, branched paraffins, aromatic hydrocarbons and sulfur-containing compounds without catalyzing reactions of the olefinic feed materials. The adsorbent is first treated with an acid and subsequently treated with a base to remove residual acidity, e.g., from the adsorbent itself or from the binder, such as silica, so as to reduce acid catalytic activity.

Neuzil et al U.S. Pat. No. 4,455,445 discloses the separation of normal $C_4$ hydrocarbons from isobutylene with silicalite adsorbent. The adsorbed normal $C_4$ hydrocarbons are desorbed with pentene-1. The patentees also suggest advantages of diluting the desorbent with a material which will not be selectively retained by the molecular sieve (i.e., not capable of acting as a desorbent), e.g., iso-octane.

Kulprathipanja et al U.S. Pat. No. 4,486,618 discloses the separation of normal $C_6$ olefins from $C_6$ branched-chain olefins and $C_6$ cyclic hydrocarbons with crystalline silica molecular sieves and recovering normal $C_6$ olefins by desorption with pentene-1 or butene-1. Iso-octane may be mixed with the desorbent to function as a carrier and diluent.

The invention herein can be practiced in fixed or moving adsorbent bed systems, but the preferred system for this separation is a countercurrent simulated moving bed system, such as described in Broughton U.S. Pat. No. 2,985,589, incorporated herein by reference. Cyclic advancement of the input and output streams can be accomplished by a manifolding system or by rotary disc valves, which are also known, e.g., shown in U.S. Pat. Nos. 3,040,777 and 3,422,848. Equipment utilizing these principles are familiar, in sizes ranging from pilot plant scale (deRosset U.S. Pat. No. 3,706,812) to commercial scale in flow rates from a few cc per hour to many thousands of gallons per hour.

The functions and properties of adsorbents and desorbents in the chromatographic separation of liquid components are well known, but for reference thereto, Zinnen et al U.S. Pat. No. 4,642,397 is incorporated herein.

We have discovered that certain desorbents are superior to the olefin desorbents of the prior art in the separation of normal and branched-chain olefinic products and the recovery of the product streams from the adsorbent, silicalite, used to separate the products. With this combination of adsorbent and desorbent, normal olefins are selectively adsorbed relative to branched-chain olefins and cyclic olefins in the feed and the adsorbed normal olefins can be desorbed. This desorbed extract stream is a valuable product which can be used for the production of alcohols. The relatively non-adsorbed branched-chain olefins and cyclic olefins are eluted as raffinate, and are also useful products, e.g., for making synthetic elastomers and as blending agents for gasoline.

SUMMARY OF THE INVENTION

The present invention is a process for separating normal olefins from a mixture of the said normal olefins with branched-chain olefins having 5 to 8 carbon atoms comprising contacting said mixture at adsorption conditions with a molecular sieve comprising crystalline silica having a silica to alumina mole ratio of at least about 700 to selectively adsorb said normal olefins, removing said relatively non-adsorbed branched-chain olefins from contact with said molecular sieve and recovering said normal olefins by desorption at desorption conditions with a desorbent consisting essentially of alkyl-substituted cycloparaffins. The preferred desorbent is methylcyclohexane. Other embodiments of our invention encompass details about feed mixtures, adsorbents, desorbent materials and operating conditions, all of which are hereinafter disclosed in the following discussion.

BRIEF DESCRIPTION OF THE DRAWINGS

FIG. 1 is the chromatographic plot of the separation of linear pentenes from branched-chain $C_5$ olefins conducted in Example I.

FIG. 2 is the chromatographic plot representing the pulse test of Example II.

DETAILED DESCRIPTION OF THE INVENTION

The preferred adsorbents for this separation are the high silica zeolites having a silica:alumina mole ratio of at least about 700, including ZSM-5 and silicalite, and a pore size of about 6 Angstroms in diameter. Such zeolites, and their preparation, are well known, for example, from U.S. Pat. Nos. 4,309,281 to Dessau and U.S. Pat. Nos. 4,061,724 and 4,104,294 to Grose et al. A more detailed discussion of silicalite may be found in the article, "Silicalite, A New Hydrophobic Crystalline Silica Molecular Sieve;" Nature, Vol. 271, Feb. 9, 1978, incorporated herein by reference. Also useful are fluoride silicalites, such as those described in U.S. Pat. No. 4,073,865 to Flanigen et al. The fluoride silicalites have a pore diameter of about 6 Angstroms. Fluoride silicalites are preferred because they are exceptionally inert and do not catalyze olefinic reactions. The silicalites used in the separation process of the invention have silica to alumina ratios ($SiO_2/Al_2O_3$) of at least 700 and preferably in the range of 700 to 1000. The base-treated adsorbents disclosed in EP 0 372 938 and EP 0 372 939, supra, are also reportedly effective in reducing acid catalytic activity and may also be used in the invention. A particularly preferred adsorbent is prepared by loading silica bonded silicalite with sodium bicarbonate prior to calcination at 850° C.

The particularly preferred adsorbent is silicalite, bonded with a binder material, such as silica, which is an amorphous material having channels and cavities thereby enabling liquid access to the adsorbent. The binder aids in forming or agglomerating the crystalline particles of the silicalite which otherwise would comprise a fine powder.

The silicalite molecular sieve may then be formed into particles such as extrudates, aggregates, tablets, macrospheres or granules having a desired particle range, preferably from about 16 to about 60 mesh (Standard U.S. Mesh) (1.9 mm to 230 $\mu$m).

Colloidal amorphous silica is an ideal binder for silicalite in that it exhibits no reactivity with olefins in the feed. A silica marketed by DuPont Co. under the trademark Ludox and another marketed by Nalco Chemical Co. (1034) are preferred. The silicalite powder is dispersed in the colloidal amorphous silica which is then gelled and may be further treated in a manner so as to substantially eliminate hydroxyl groups, such as by thermal treatment in the presence of oxygen at a temperature from about 450° C. to about 1000° C. for a minimum period from about 3 hours to about 48 hours. The silicalite should be present in the silica matrix in amounts ranging from about 75 wt. % to about 98 wt. % silicalite based on volatile-free composition.

The extruded bonded silicalite particles are thoroughly mixed with a solution of a soluble sodium compound, such as sodium bicarbonate, sodium phenoxide, sodium methoxide, sodium hyponitrite, sodium iodate, sodium tartrate, sodium thiosulfate, potassium hypochlorite, potassium carbonate, potassium nitride, potassium oxalate, potassium succinate, rubidium bicarbonate, rubidium dichlorobromide and rubidium sulfate. Finally, the mixture is dried and calcined at a temperature of least 700° C., up to about 1000° C., preferably in the range 800° C. to 900° C. This adsorbent has been determined to be virtually non-reactive under conditions of the adsorption separation of the invention (i.e., no formation of heavy products when feed is contacted with the adsorbent overnight in a pressure vessel, such as Parr bomb, at 175° C.).

The adsorbent may be employed in the form of a dense fixed bed which is alternately contacted with a feed mixture and a desorbent material in which case the process will be only semicontinuous. In another embodiment a set of two or more static beds of adsorbent may be employed with appropriate valving so that a feed mixture can be passed through one or more adsorbent beds of a set while a desorbent material can be passed through one or more of the other beds in a set. The flow of a feed mixture and a desorbent material may be either up or down through an adsorbent in such beds. Any of the conventional apparatus employed in static bed fluid-solid contacting may be used.

Separation processes employing countercurrent moving-bed or simulated moving-bed countercurrent flow systems, however, have much greater separation efficiencies than do separation processes employing fixed adsorbent bed systems. With the moving-bed or simulated moving-bed flow systems a feed mixture and a desorbent material are continuously fed to the process and adsorption and desorption are continuously taking place which allows continuous production of an extract output stream and a raffinate output stream. In a preferred embodiment, therefore, the process will use such flow systems. In a more preferred embodiment, the process will employ a simulated moving-bed countercurrent flow system. The operating principles and sequence of operation of one such simulated moving-bed countercurrent flow system are described in U.S. Pat. No. 2,985,589 incorporated herein by reference.

The separation process of the invention can be practiced using any feed containing a mixture of normal olefins and branched-chain olefins having from 5 to 8 carbon atoms. The olefins may be narrow boiling point fractions, such as $C_5$ to $C_6$, etc., or may have a single carbon number, e.g., pentenes, hexenes, heptenes, octenes, etc. In a preferred process, any paraffins are removed first so that one product of the separation is substantially pure linear olefins and the other product is branched-chain olefins. The paraffins can be removed by an adsorptive separation such as described above (known as the Olex Process, a service mark of UOP) using a sodium-exchanged X zeolite. The olefins (linear and branched) are desorbed and recovered from the extract stream after removing a raffinate stream containing the paraffins. The paraffin-containing raffinate mixture may be separated into normal and iso-paraffin streams by a similar adsorptive separation process, known as Molex, a service mark of UOP, using a Linde 5 A zeolitic molecular sieve (available from UOP) and a liquid paraffinic desorbent having a boiling point different from the feed. The feed to the Olex Process stage of the three-stage separation described in this paragraph can be a dimerized $C_5$ cut from a steam-cracked hydrocarbon from which cyclopentadiene has been removed by dimerization and isoprene has been removed by solvent extraction. The extract from the Olex stage contains normal and branched-chain olefins and becomes the feed for the separation process of the invention.

Other sources of feed mixture which may be separated by the process of the invention are: olefinic streams from catalytic cracking and Fischer-Tropsch reactions.

The preferred desorbents for use in the process for separating normal olefins from non-normal olefins, i.e., branched-chain and cyclic olefins, are alkyl-substituted cyclic paraffins having from $C_6$ to $C_8$ carbon atoms and boiling points at least 5° C. higher or lower than the feed material so that the desorent can be easily recovered for reuse. A preferred desorbent for separating lower olefins, e.g., butenes, pentenes and hexanes is methylcyclohexane (b.p. 101° C.). A preferred desorbent for separating higher olefins, e.g., n-octenes from isooctenes, is methylcyclopentane (b.p. 72° C.). Others include ethylcyclopentane (b.p. 103° C.), ethylcyclohexane (b.p. 130°–132° C.), propylcyclopentane (130.9° C.) and dimethylcyclohexane (b.p. 119°–121° C.).

The general scheme for adsorptive separations is known from the aforesaid U.S. Pat. No. 2,985,589. Briefly, the less adsorbed feed component(s) is eluted from the non-selective void volume and weakly adsorbing volume before the more strongly adsorbed component(s). The relatively unadsorbed component(s) is thereby recovered in the raffinate. The relatively adsorbed component(s) is desorbed and recovered in the extract.

Although both liquid and vapor phase operations can be used in many adsorptive separation processes, liquid-phase operation is preferred for this process because of the lower temperature requirements and because of the higher yields of extract product that can be obtained with liquid-phase operation over those obtained with vapor phase operation. Adsorption conditions will include a temperature range of from about 25° C. to about 200° C. and a pressure sufficient to maintain liquid-phase, ranging from about atmospheric to about 400 psig, with from about atmospheric to about 200 psig usually being adequate. Desorption conditions will include the same range of temperatures and pressures as used for adsorption conditions.

At least a portion of the raffinate stream, which contains the concentrated branched-chain olefin product, and at least a portion of the extract stream, which contains the normal olefin product, from the separation process are passed to separation means, typically fractionators or evaporators, where at least a portion of desorbent material is separated to produce a raffinate product and an extract product, respectively. The desorbent material is normally recycled to the adsorption column where it is combined with fresh desorbent.

A dynamic testing apparatus is employed to test various adsorbents with a particular feed mixture and desorbent material to measure the adsorption characteristics of retention, capacity and exchange rate. The apparatus consists of a helical adsorbent chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect qualitatively, or determine quantitatively, one or more components in the effluent stream leaving the adsorbent chamber. A pulse test, performed using this apparatus and the following general procedure, is used to determine data, e.g., selectivity, for various adsorbent systems. The adsorbent is placed in a chamber and filled to equilibrium with a particular desorbent material by passing the desorbent material through the adsorbent chamber. At a convenient time, a pulse of feed containing known concentrations of a tracer such as mesitylene is injected for a duration of several minutes. Desorbent material flow is resumed, and the tracer or the raffinate component (or both) and the extract component are eluted as in a liquid-solid chromatographic operation. The effluent can be analyzed on-stream, or, alternatively, effluent samples can be collected periodically and later analyzed separately by analytical equipment and traces of the envelopes or corresponding component peaks developed.

From information derived from the test, adsorbent performance can be rated in terms of void volume, retention volume for an extract or a raffinate component, the rate of desorption of an extract component from the adsorbent and selectivity. The retention volume of an extract or a raffinate component may be characterized by the distance between the center of the peak envelope of the extract or raffinate component and the center of the peak envelope of the tracer component (void volume) or some other known reference point. It is expressed in terms of the volume in cubic centimeters of desorbent material pumped during this time interval represented by the distance between the peak envelopes. The rate of exchange or desorption rate of an extract component with the desorbent material can generally be characterized by the width of the peak envelopes at half intensity. Selectivity, $\beta$, is determined by the ratio of the net retention volumes of the more strongly adsorbed component to each of the other components.

The examples shown below are intended to further illustrate the process of this invention without unduly limiting the scope and spirit of said process.

EXAMPLE I

A pulse test as described above was performed to evaluate the process of the present invention for separating a mixture of normal and branched-chain $C_5$ olefins. The column was filled with 70 cc of a modified (sodium silicate) silicalite adsorbent, prepared by an after treatment which eliminates catalytic activity of the adsorbent for olefins. The precursor was silicalite (S-115 available from UOP) with a silica binder (Nalco 1034a). The after treatment consisted of mixing ⅛-inch silicalite extrudate with a 0.5% (wt.) solution of sodium bicarbonate and drying at 550° C. for 1 hour and calcining at 840° C. for 1 hour. The separation column was maintained at a temperature of 160° C. and a pressure sufficient to provide liquid-phase operations. The sample was 2 cc of a mixture which contained 20% (wt.) mesitylene (tracer) and 80% (wt.) of feed having the approximate composition shown in Table 1 below.

The desorbent was methylcyclohexane. The desorbent material was run continuously at a nominal liquid hourly space velocity (LHSV) of 1 (1.36 ml per minute flow rate). At some convenient time interval, the desorbent was stopped and the feed mixture was run for a 1.5 minute interval at a rate of 1.36 ml/min. The desorbent stream was then resumed at 1 LHSV and continued to pass into the adsorbent column until all of the feed components had been eluted from the column as determined by analyzing the effluent stream leaving the adsorbent column. The results of the analyses obtained are shown in FIG. 1. The branched-chain olefins are removed as raffinate near the void volume and the normal olefins are desorbed thereafter. A small amount of n-pentane impurity in the feed was found in the extract. The results are also set forth in the following Table 1 of gross retention volumes (GRV), net retention volumes (NRV) and selectivities ($\beta$).

TABLE 1

| Component | Wt. % in Feed | GRV (ml.) | NRV (ml.) | $\beta$ |
|---|---|---|---|---|
| Mesitylene | — | 38.9 | 0.0 | ∞ (Tracer) |
| 2-Methyl-2-Butene | 41.19 | 40.2 | 1.3 | 17.64 |
| 2-Methyl-1-Butene | 8.38 | 40.8 | 1.9 | 12.70 |
| 3-Methyl-1-Butene | 0.28 | 41.3 | 2.4 | 10.10 |
| Cyclopentene | 2.63 | 42.8 | 3.9 | 6.6 |
| n-Pentane | 0.16 | 53.3 | 14.4 | 1.66 |
| Cis-2-Pentene | 16.62 | 53.5 | 14.6 | 1.63 |
| Trans-2-Pentene | 25.17 | 61.4 | 22.5 | 1.06 |
| Pentene-1 | 4.94 | 62.7 | 23.8 | 1.00 (Ref.) |

EXAMPLE II

A $C_6$ olefin feed having the composition in Table 2 was separated in a pulse test in the same manner as in Example I using another sample of sodium silicate prepared in the same way as Example I. The column was filled with 70 cc of adsorbent and maintained at a temperature of 160° C. and operated in the same manner and under the same conditions as in Example I. The sample was 2 cc of a mixture which contained 20% (wt.) mesitylene and 80% (wt.) of a feed having the approximate composition shown in Table 2 below. The desorbent was methylcyclohexane. The analysis of the eluents was made in the same way as in Example I and the results are shown in Table 2 and FIG. 2.

TABLE 2

| Component | Feed Composition Wt. % | GRV (ml.) | NRV (ml.) | β |
|---|---|---|---|---|
| Mesitylene | — | 44.5 | 0.0 | ∞ (Tracer) |
| 3-Methylpentane | 4.9 | 45.4 | 0.9 | 21.48 |
| 2-Methyl-1-pentene | 5.8 | 45.5 | 1.1 | 18.62 |
| 3-Methylcyclopentene | 0.9 | 45.8 | 1.3 | 14.84 |
| 2 Ethyl-1-butene | 1.1 | 46.2 | 1.8 | 11.06 |
| 2-Methyl-2-pentene | 0.9 | 46.2 | 1.8 | 11.06 |
| Hexene-1 | 86.4 | 64.2 | 19.7 | 1.00 |
| 2-Methyl-2-pentene | 0.9 | 46.2 | 1.8 | 11.06 |

From the above, it can be seen that hexene-1 was well-separated from the branched-chain hexenes.

EXAMPLE III

A commercially-available source of $C_8$ olefins was separated in a pulse test in the same manner as in Example I using the same adsorbent. The temperature in the column was 120° C. and was operated under the same conditions. The desorbent was methylcyclopentane. The sample was 2 cc of a mixture of 80% (wt.) of the octene feed composition shown in Table 3 and 20% (wt.) of mesitylene as the tracer. Because of difficulty in analyzing individual components in this complex feed mixture, the eluents were hydrogenated and then analyzed by gas chromatography (GC) for the boiling points of the following groups as paraffins: dialkyl $C_8$ olefins; monoalkyl $C_8$ olefins and normal olefins. The dialkyl $C_8$ olefins include 2,4- and 3,4-dimethylhexene and 3-methyl-3-ethylpentene. The monoalkyl $C_8$ olefins include 3-methylheptene and 3-ethylhexene. The results are shown in the following Table 3.

TABLE 3

| Component | Wt. % in Feed | GRV (ml) | NRV (ml) | β |
|---|---|---|---|---|
| Mesitylene | — | 50.5 | 0.0 | ∞ (Tracer) |
| Dialkyl $C_8$ Olefins | 31.3 | 50.2 | −0.2 | — |
| Monoalkyl $C_8$ Olefins | 49.1 | 57.5 | 7.0 | 5.75 |
| Normal Octenes | 16.7 | 90.9 | 40.4 | 1.00 (Ref.) |

The linear (normal) octenes were easily separated from the branched olefins in the feed.

EXAMPLE IV

The pulse test separation of Example III was repeated with the same feed and the same adsorbent. In this example, the column was operated at a temperature of 100° C. The desorbent was methylcyclohexane. The results are set forth in the following Table 4.

TABLE 4

| Component | GRV (ml) | NRV (ml) | β |
|---|---|---|---|
| Mesitylene | 44.9 | 0.0 | ∞ (Tracer) |
| Dialkyl $C_8$ Olefins | 44.6 | −0.3 | — |
| Monoalkyl $C_8$ Olefins | 45.3 | 0.4 | 6.86 |
| Normal Octenes | 47.8 | 2.9 | 1.00 (Ref.) |

The linear olefins were again separated from branched olefins, although more tailing was evident with methylcyclohexane as the desorbent.

EXAMPLE V

This example illustrates the ability of our process, when operated in a preferred embodiment, which utilizes a continuous simulated moving bed countercurrent type of operation, and comprises a pilot plant scale testing apparatus known as a carousel unit described in detail in deRosset et al. U.S. Pat. No. 3,706,812, incorporated herein by reference. Briefly, the apparatus consists essentially of 24 serially connected adsorbent chambers having about 19.2 cc volume each. Total chamber volume of the apparatus is approximately 460 cc. The individual adsorbent chambers are serially connected to each other with relatively small diameter connecting piping and to a rotary type valve with other piping. The valve has inlet and outlet ports which direct the flow of feed and desorbent material to the chambers and extract and raffinate streams from the chambers. By manipulating the rotary valve and maintaining given pressure differentials and flow rates through the various lines passing into and out of the series of chambers, a simulated countercurrent flow is produced. The adsorbent remains stationary while fluid flows throughout the serially connected chambers in a manner which when viewed from any position within the adsorbent chambers is steady countercurrent flow. The moving of the rotary valve is done in a periodic shifting manner to allow a new operation to take place in the adsorbent beds located between the active inlet and outlet ports of the rotary valve. Attached to the rotary valve are input lines and output lines through which fluids to and from the process flow. The rotary valve contains a feed input line through which passes the feed mixture, and extract stream outlet line through which passes the extract product admixed with desorbent material, a desorbent material inlet line through which passes desorbent materials and a raffinate stream outlet line through which passes the raffinate product in admixture with desorbent material. Additionally, a flush material inlet line is used to admit flush material for the purpose of flushing feed components from lines which had previously contained feed material and which will subsequently contain the raffinate or extract stream. The flush material employed was mesitylene (although desorbent would normally be used) which then leaves the apparatus as part of the extract stream and raffinate stream. Additional apparatus and process control details can be found in U.S. Pat. No. 3,706,812.

The feed mixture to the apparatus was the $C_5$ olefin mixture of Example I. The adsorbent used was the same as in Example I. The desorbent was methylcyclohexane.

A number of experiments, each of six hours duration, were conducted on the carousel unit. In these experiments it was observed that the linear pentenes were adsorbed by the adsorbent and so were separated with the extract, while the non-linear $C_5$ olefins were relatively unadsorbed and so were separated with the raffinate.

In these experiments, the extract and raffinate streams were analyzed for their linear and non-linear pentene content, respectively. The separation process resulted in extract purities of greater than about 96% at recoveries in excess of 90%.

EXAMPLE VI

A second pilot plant scale separation was made on a $C_6$ olefin feed in the same manner as in Example V, using the same adsorbent and desorbent. The feed to the continuous countercurrent simulated moving bed apparatus was the same as in Example II. The extract stream was analyzed for linear hexenes and purities were obtained which were greater than 99% at recoveries greater than 95%.

What is claimed:

1. A process for separating normal olefins from a mixture of the said normal olefins and branched-chain olefins having 5 to 8 carbon atoms comprising contacting said mixture at adsorption conditions with a molecular sieve having low acid catalytic reactivity comprising crystalline silica having a silica to alumina mole ratio of at least about 700 to selectively adsorb said normal olefins, removing said relatively non-adsorbed branched-chain olefins from contact with said molecular sieve and recovering said normal olefins by desorption at desorption conditions with a desorbent consisting essentially of alkyl-substituted cycloparaffins.

2. The process of claim 1 wherein said desorbent is selected from the group consisting of methylcyclopentane, methyl-ethylcyclopentane, ethylcyclohexane, propylcyclopentane and dimethylcyclohexane.

3. The process of claim 1 wherein said desorbent is methylcyclopentane.

4. The process of claim 1 wherein said desorbent is methylcyclohexane.

5. The process of claim 1 wherein said adsorbent is a fluoride silicalite.

6. The process of claim 1 wherein said adsorbent is silicalite or ZSM-5.

7. The process of claim 1 wherein said adsorbent has been treated to reduce acid catalytic activity.

8. The process of claim 1 wherein said normal olefins and branched-chain olefins have 6 carbon atoms.

9. The process of claim 1 wherein said normal olefins and branched-chain olefins have 8 carbon atoms.

* * * * *